US00PP37228P2

(12) United States Plant Patent
Weber

(10) Patent No.: US PP37,228 P2
(45) Date of Patent: Jan. 27, 2026

(54) RASPBERRY PLANT NAMED 'Crimson Blush'

(50) Latin Name: ***Rubus idaeus* L**
Varietal Denomination: Crimson Blush

(71) Applicant: Cornell University, Ithaca, NY (US)

(72) Inventor: Courtney Weber, Geneva, NY (US)

(73) Assignee: Cornell University, Ithaca, NY (US)

( * ) Notice: Subject to any disclaimer, the term of this patent is extended or adjusted under 35 U.S.C. 154(b) by 0 days.

(21) Appl. No.: 19/224,394

(22) Filed: May 30, 2025

(51) Int. Cl.
*A01H 5/08* (2018.01)
*A01H 6/74* (2018.01)

(52) U.S. Cl.
USPC ..... Plt./204

(58) Field of Classification Search
USPC ..... Plt./204
See application file for complete search history.

(56) References Cited

U.S. PATENT DOCUMENTS

| | | | | |
|---|---|---|---|---|
| PP10,412 | P | 5/1998 | Swartz et al. | |
| PP12,173 | P2 | 10/2001 | Swartz et al. | |
| PP23,375 | P3 | 2/2013 | Weber | |
| PP32,799 | P2 * | 2/2021 | Weber | A01H 5/08 Plt./204 |

* cited by examiner

*Primary Examiner* — Susan McCormick Ewoldt
*Assistant Examiner* — Zachariah Allan Kay
(74) *Attorney, Agent, or Firm* — Foley & Lardner LLP

(57) ABSTRACT

This invention relates to a new and distinct primocane bearing red raspberry plant designated as 'Crimson Blush' primarily adapted to growing conditions of west central New York and other regions of similar climate. The new plant is primarily characterized by very tall canes, conical fruit that is longer than broad, a late season primocane production period, concentrated display of fruit and light red fruit color.

5 Drawing Sheets

STATEMENT REGARDING FEDERALLY SPONSORED RESEARCH OR DEVELOPMENT

Figure 1A:
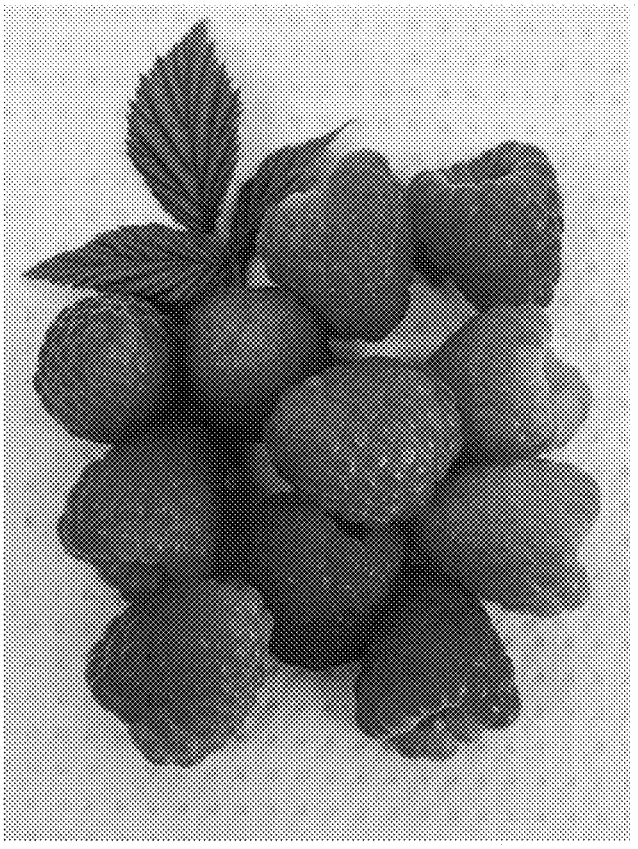

This invention was made with government support under NI20HFPXXXXXG054 awarded by the National Institute of Food and Agriculture. The government has certain rights in the invention.

Latin name of the genus and species of the plant claimed: *Rubus idaeus* L.

Variety demonination: 'CRIMSON BLUSH'

BACKGROUND OF THE INVENTION

The present invention relates to a new and distinct primocane bearing (fall bearing) red raspberry plant designated as 'Crimson Blush'. The plant is botanically known as *Rubus idaeas* L. The new and distinct red raspberry originated from a hand-pollinated cross of the Cornell selection NY11-25 (unpatented) and Cornell selection NY12-14 (unpatented). This cross was made and the resulting seedling grown in Geneva, New York. The seedling was selected from a controlled breeding plot in 2017 and was designated NY17-35 for testing. The new plant has been asexually propagated by dormant canes since 2018 and was established in tissue culture for propagation of plants for further trials in late 2018. This propagation has demonstrated that the combination of traits that characterize this plant are fixed and remain true to type through successive generations of asexual propagation.

SUMMARY OF INVENTION

'Crimson Blush' is primarily adapted to the climate and growing conditions of west central New York and other regions of similar temperate climate. This climate allows for the development of tall primocanes that produce mature fruit in the late fall season starting in late September extending to early December with weather protection. 'Crimson Blush' benefits from the use of protective structures such as plastic hoop houses or high tunnels, which allow for optimal cane growth and the complete harvest of the fall crop when the risk of frost is prevalent. When allowed to produce a floricane crop in the following summer, this portion of the crop is a larger percentage of the total yield with similar mean fruit weight and lesser maximum fruit weight.

The following traits have been repeatedly observed and are determined to be unique characteristics of 'Crimson Blush', which in combination distinguish this raspberry plant as a new and distinct plant:

1. Late harvest season on primocanes;
2. Primocane crop concentrated on the top ⅓ of the cane;
3. High yields especially when double cropped;
4. Very tall upright canes with low branching;
5. Bright, light red, cone shaped fruit; and
6. Sparse, short prickles on mature sections of the canes.

The new plant differs from its parents by combining the concentrated fruiting habit and large fruit size of the seed parent NY11-25 with the light red, firm fleshed fruit of the pollen parent NY12-14. NY11-25 produces large sized, conic fruit that is medium red and relatively soft that is concentrated in the top ⅓section of the primocanes. NY12-14 is less vigorous and produces a smaller crop of light red, cone shaped fruit on medium height canes. The new plant is dissimilar to other primocane fruiting varieties currently grown in New York in that the new plant has a late primocane harvest season, produces fruit on very tall canes with few branches, concentrated on the top ⅓potion of the primocane. The new plant is most similar in fruiting season and cane stature to the unpatented plant 'Heritage' which has sturdy upright primocanes that are heavily pigmented greyed-red with many stout prickles. The fruiting season of the new plant begins somewhat later than 'Heritage' and extends as much as 30 days longer into the late season when only late season varieties such as 'Crimson Giant' (U.S. Plant Pat. No. 23,375 P3) and 'Josephine' (U.S. Plant Pat. No. 12,173) had previously been productive. This is facilitated by the tall canes that do not develop flowers until later than other varieties. The canes of 'Crimson Blush' are typically lightly blushed red-purple (red-purple group 61B) over light yellow-green colored (yellow-green group 145C) when mature with short, sparse, red-purple (red-purple group 60A) colored prickles on the mature sections. The fruit of the new plant are most similar in shape to the fruit of the primocane variety 'Caroline' (U.S. Plant Pat. No. 10,412) which has large, dark red fruit that tend to be dull and that are slightly broader than long. In contrast, the fruit of the new plant are longer than the fruit of 'Caroline' and more conic in shape, are more glossy and lighter red at full maturity. The canes of 'Caroline' are variably pigmented red purple to greyed yellow, with few short prickles and a waxy coating. In comparison to the similar varieties 'Caroline' and 'Heritage' (unpatented), 'Crimson Blush' differs by the following combination of characteristics described in Table 1. Color terminology is based on The Royal Horticultural Society colour chart (2001 edition).

TABLE 1

Plant and Fruit Characteristics

| Characteristic | 'Crimson Blush' | 'Caroline' (U.S. Plant Pat. No. 10,412) | 'Heritage' (Unpatented) |
|---|---|---|---|
| 1. Mature primocane color | Red-purple 61B over Yellow-green 145C | Red purple 59B over Greyed-yellow 160A | Greyed-red 180B |
| 2. Fruit shape | Conical | Broad conical | Round |
| 3. Fruit length (mm) | 26.3 | 18 | 15 |
| 4. Fruit width (mm) | 23.3 | 19 | 14 |
| 5. Fruit length × width ratio | 1.13 | 0.9 | 1.1 |
| 6. Mean fruit weight-primocane | 3.1 g | 2.5 g | 1.9 g |
| 7. Maximum fruit weight-primocane | 6.4 g | 3.8 g | 3.0 g |
| 9. Mean fruit weight-floricane | 4.0 g | 2.2 g | 1.8 g |
| 8. Maximum fruit weight-floricane | 5.6 g | 3.5 g | 2.7 g |
| 9. Mature fruit color | Red 45A | Red 45A | Red 53A |
| 10. Canes per plant | 24 | 31 | 29 |
| 11. Fruiting laterals per primocane | 16 | 14 | 18 |
| 11. Leaflet number | Primarily 3, sometimes lobed or fused | 5 | Primarily 3 with up to 10% 5 |

BRIEF DESCRIPTIONS OF THE DRAWINGS

The color photographs illustrate typical characteristics of the new plant 'Crimson Blush' and are as true to color as reasonably possible with photographic reproductions of this type. Color in the photographs may differ slightly from the color value cited in the detailed botanical description, which accurately describes the color of 'Crimson Blush'. The photographs of canes and fruit were taken in Geneva, New York in the second year of harvesting fruit in the plot.

Figure 1B:
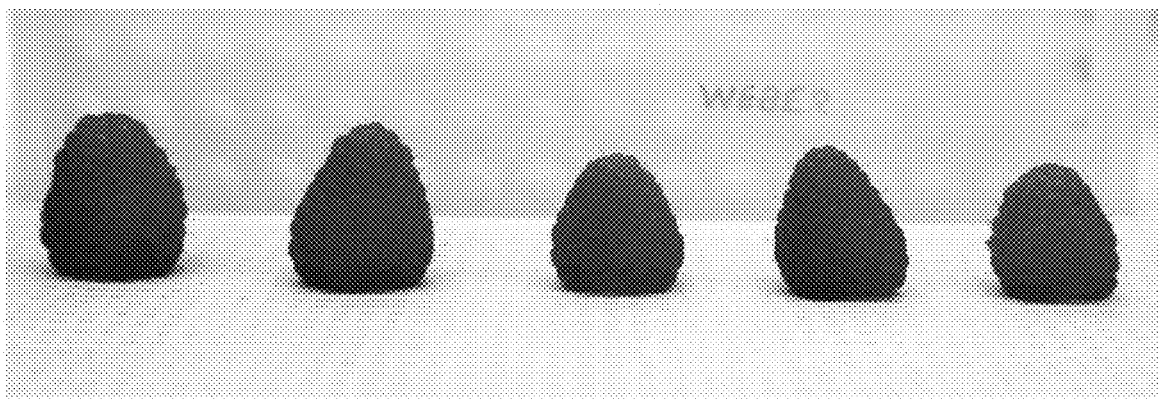

FIG. 1A—Typical fruit shape and size of 'Crimson Blush' in a container;

FIG. 1B—Side view of 'Crimson Blush'; and

Figure 1C:
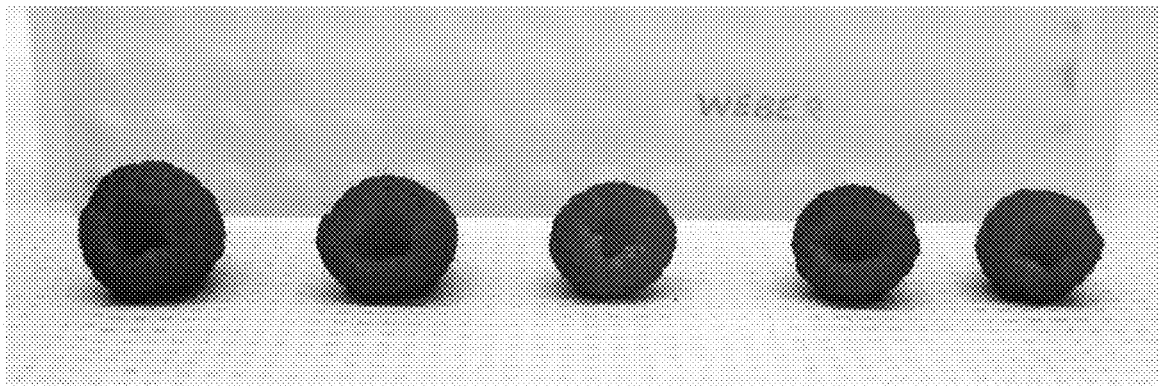

FIG. 1C—Bottom view of 'Crimson Blush' showing the cavity.

Figure 2A:
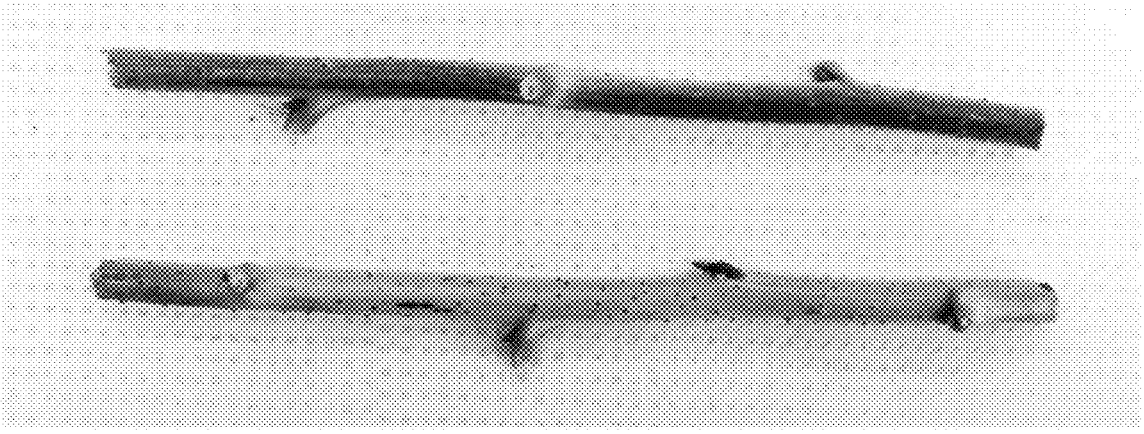
Figure 2B:
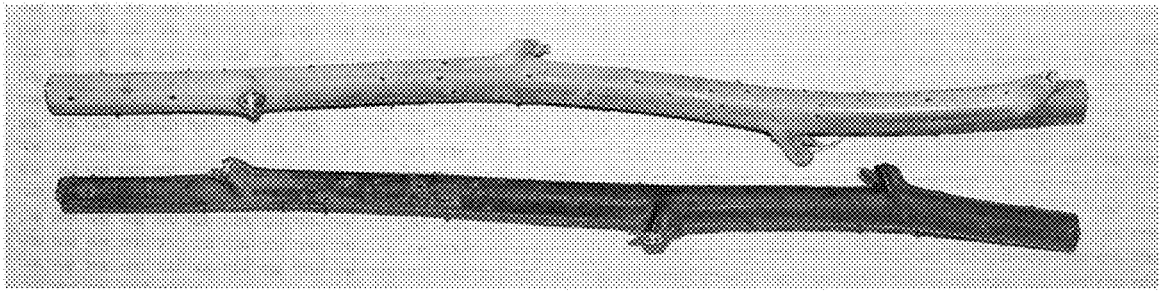
Figure 2C:
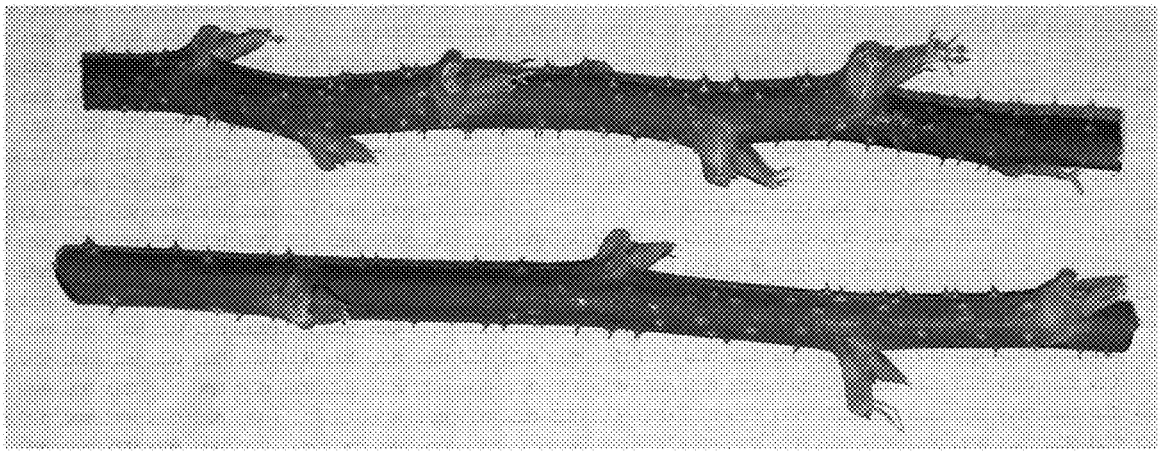

FIG. 2A—Typical primocane pigmentation and spine density of mature canes for 'Crimson Blush';

FIG. 2B—Typical primocane pigmentation and spine density of mature canes for 'Caroline'; and FIG. 2C—Typical primocane pigmentation and spine density of mature canes for 'Heritage'.

Figure 3A:
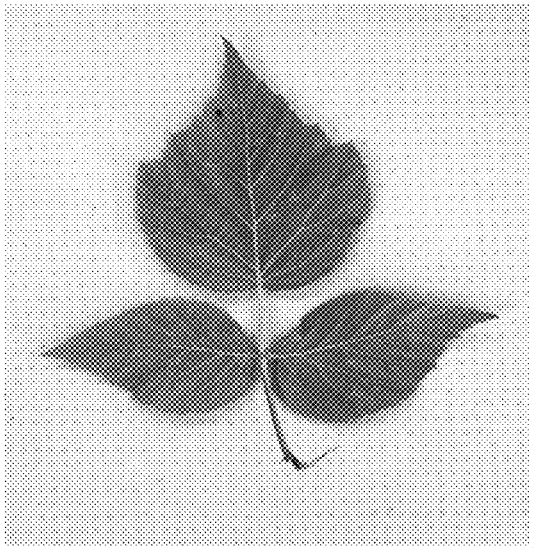
Figure 3B:
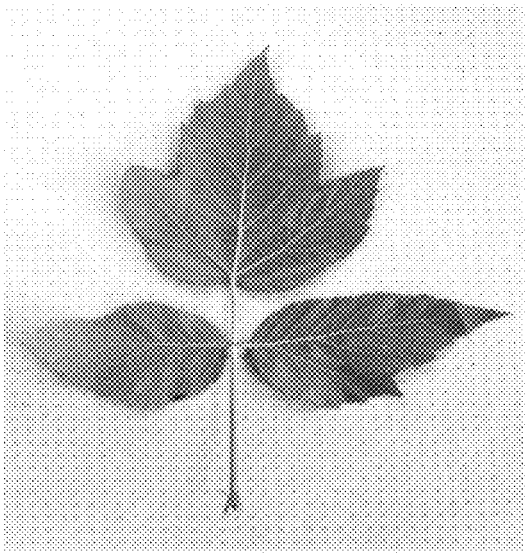

FIG. 3A—Typical three leaflet mature leaflet arrangements found on 'Crimson Blush';

FIG. 3B—Typical three leaflets with lobed terminal leaflet; and

Figure 3C:
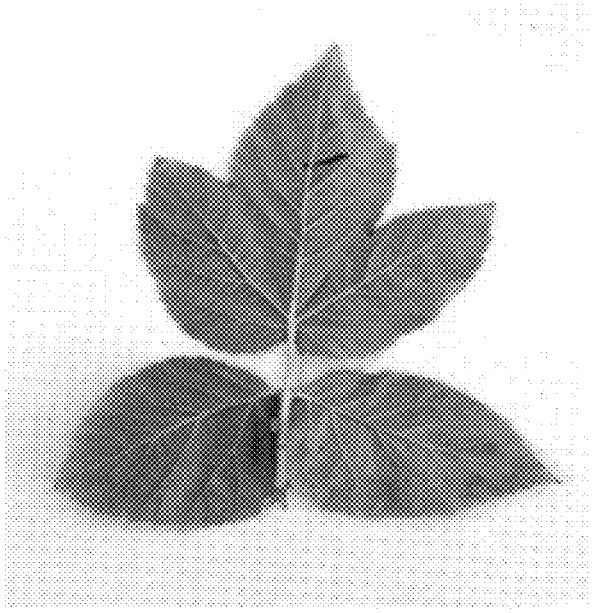

FIG. 3C—Typical three leaflets with terminal leaflet fused with secondary leaflets.

Figure 4:
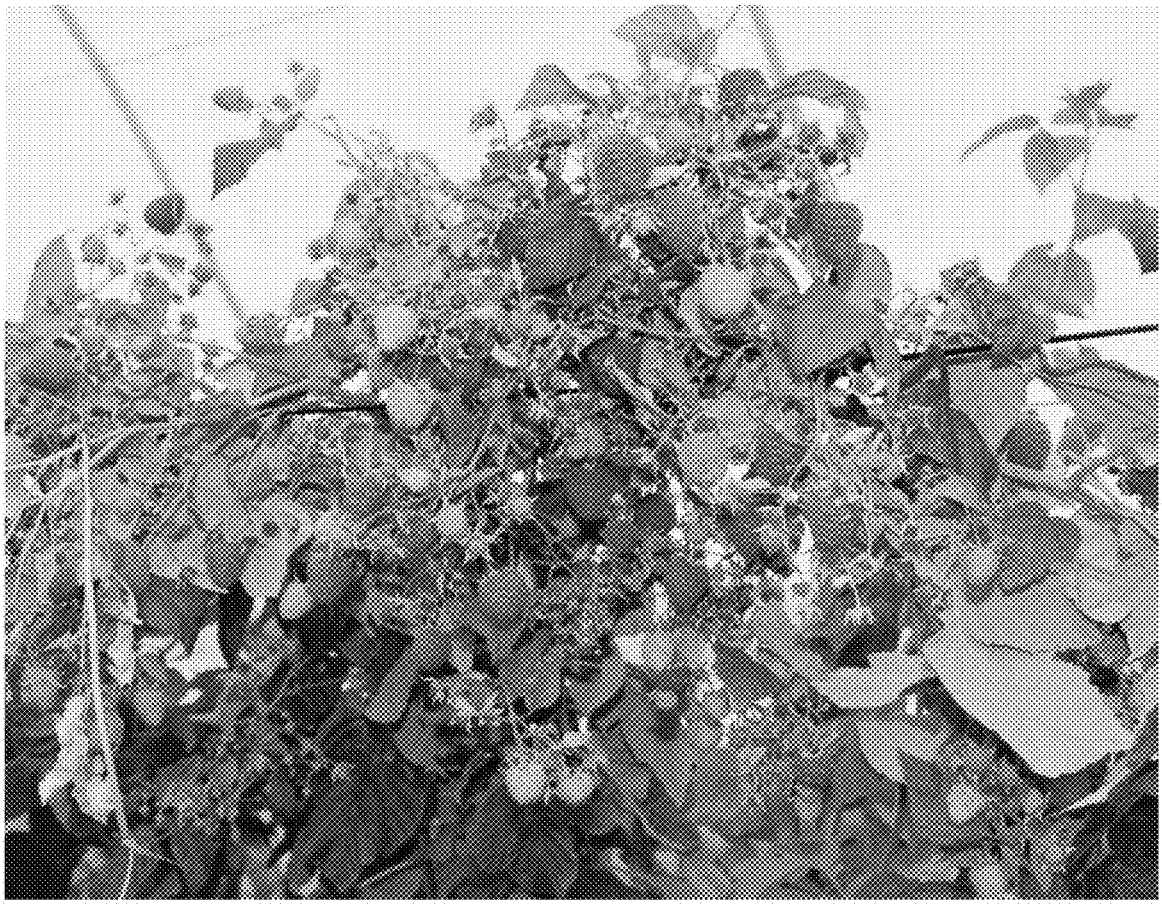

FIG. 4—Fruiting habit of 'Crimson Blush' showing concentrated display of fruit on top portion of the cane.

DETAILED BOTANICAL DESCRIPTION

'Crimson Blush' has not been observed under all possible environmental conditions and as such the characteristics may vary in detail depending on weather conditions, day length, soil type and location.

The photographs together with the description of the new raspberry 'Crimson Blush' are based upon the observations taken during the 2023-24 growing seasons in Geneva, NY. Measurements were taken on plants grown in the soil in a perennial planting in a high tunnel system that was planted in Geneva, New York in 2022 with the canes emerging naturally in late April each year. Flower measurements and characteristics were taken from primary flowers and fruit measurements from primary and secondary fruit. Mean measurements of fruit size were taken on 10 fruit samples throughout the season. Measurements of flower and fruit parts are means of 10 samples. Cane measurements and spine density taken within the center third of the cane unless otherwise noted.

Classification:

*Family*—Rosaceae.

*Botanical*—*Rubus idaeus* L.

*Common name*—Red Raspberry.

Parentage: NY11-25 (Unpatented) x NY12-14 (unpatented).

Plant:

*Propagated*—asexual dormant canes, tissue culture.

Primocanes:

*Cane color*—Yellow-green 145C with red-purple 61B blush.

*Prickles*—present.

*Cane length*—2.3-2.5 m; mean 2.4 m.

*Cane diameter*—8-10 mm; mean 9 mm.

*Number of fruiting lateral branches*—15-18; mean 16.

*Maximum fruiting lateral length*—116 cm.

*Cane pubescence*—none.

Prickles:
*Density*—moderate at base, low at middle third.
*Form*—thin.
*Length*—short-1 mm mean.
*Apex*—straight downward.
*Color*—red-purple 60A on mature canes.

Leaves:
*Type*—compound; typically 3 leaflets; approximately 15% secondary leaflet(s) fused with terminal leaflet or fused with other secondary leaflets.
*Mature leaflet color*—upper surface Green 143A; lower surface Gray-green 191C.
*Arrangement*—Free.
*Terminal leaflet length*—10.4-12.3 cm; mean 11.7 cm.
*Terminal leaflet width*—6.8-8.8 cm; mean 7.9 cm.
*Terminal leaflet length to width ratio*—1.5.
*Basal leaflet length*—10.6-11.8 cm; mean 11.1 cm.
*Basal leaflet width*—7.0-8.8 cm; mean 7.8 cm.
*Basal leaflet length to width ratio*—1.4.
*Leaflet shape*—ovate.
*Terminal leaflet tip*—acuminate.
*Basal leaflet attachment*—cuspidate.
*Leaflet margins*—doubly serrate.
*Terminal leaflet number of serrations*—95 mean.
*Basal leaf attachment*—cordate to auriculate.
*Leaflet overlap*—none.
*Petiole length*—6.6 cm.
*Petiole width*—7.7 mm.
*Petiole prickles*—present, sparse.
*Petiole prickles apex*—slight downward toward stem.
*Petiole color*—Yellow-green 145C.

Stipules:
*Quantity per leaf*—2.
*Shape*—straight and erect.
*Length*—6.6-9 mm; mean 7.8 mm.
*Color*—Yellow-green 145C.

Flowers:
*Diameter*—2.1-3.1 cm; mean 2.7 cm.
*Bud shape*—conical.
*Fragrance*—none.
*Petals number*—typically 5, occasionally 6 or 7 in primary flowers.
*Petal shape*—obovate.
*Petal length*—6.5-9 mm; mean 7.6 mm.
*Petal width*—3-4 mm; mean 3.3 mm.
*Petal length to width ratio*—2.3.
*Petal color*—White 155C.
*Sepal number*—typically 5; sometimes 6 in primary flowers.
*Sepal length*—11-15.5 mm; mean 14.1 mm.
*Sepal color*—upper surface Yellow-green 144D; lower surface Yellow-green 144A.
*Mean stigma number*—142.
*Stigma color*—White 155B.
*Mean stamen number*—95.
*Anther color*—White 155A.
*Anther filament color*—White 155D.
*Stamen height*—below stigmatic surface.

Fruit:
*Shape*—broad conic.
*Fruit length*—2.0-3.2 cm; mean 2.6 cm.
*Fruit width*—1.7-2.8 cm; mean 2.3 cm.
*Fruit length to width ratio*—1.13.
*Weight-primocane*—4.2-7.1 g; mean 4.9 g.
*Weight-floricane*—3.4-5.6 g; mean 4.0 g.
*Number of drupelets*—134 for mean primocane fruit size.
*Color of harvest mature fruit*—Orange-red group 35A.
*Color of fully mature fruit*—Red group 45A.
*Pedicel diameter*—1 mm.
*Pedicel spines*—present; moderate number; curved back towards cane.
*Adherence to receptacle*—medium.

Pest and Disease Reactions:
*Spotted wing drosophila* (*Drosophila suzukii*)—Susceptible.
*Two spotted spider mite* (*Tetranychus urticae*)—Susceptible.
*Grey fruit mold* (*Botrytis cinerae*)—Susceptible.
*Powdery mildew* (*Podosphaera aphanis var. aphonic*)—susceptible.
*Yellow rust* (*Phragmidium rubi-idaei*)—resistant.

I claim:

1. A new and distinct raspberry plant named 'Crimson Blush', as herein described and illustrated by the characteristics set forth above.

* * * * *